United States Patent [19]

Stout et al.

[11] Patent Number: 4,666,924
[45] Date of Patent: May 19, 1987

[54] CERTAIN PYRIDYL SUBSTITUTED AMINOMETHYL BENZENE DERIVATIVES HAVING ANTI-ARRHYTHMIC ACTIVITY

[75] Inventors: David M. Stout, Vernon Hills; William L. Matier, Libertyville, both of Ill.

[73] Assignee: E. I. Du Pont de Nemours & Co., Wilmington, Del.

[21] Appl. No.: 617,286

[22] Filed: Jun. 4, 1984

Related U.S. Application Data

[62] Division of Ser. No. 401,752, Jul. 26, 1982, Pat. No. 4,466,965.

[51] Int. Cl.$^4$ .............. C07D 401/12; C07D 401/14; A61K 31/44; A61K 31/445
[52] U.S. Cl. .................... 514/343; 514/255; 514/227; 514/228; 514/318; 544/60; 544/82; 544/360; 546/187; 546/281; 546/309; 546/310; 546/312; 546/316; 546/323
[58] Field of Search .............. 546/281, 187, 309, 310, 546/312, 316, 323; 544/60, 82, 360; 514/318, 255, 343, 228, 227

[56] References Cited

U.S. PATENT DOCUMENTS

| | | | |
|---|---|---|---|
| 3,240,781 | 3/1966 | Turner et al. | 544/237 |
| 4,466,965 | 12/1984 | Stout et al. | 514/236 |
| 4,562,201 | 12/1985 | Stout et al. | 514/422 |

OTHER PUBLICATIONS

Sun et al., ACTA Pharmaceutica Sinica, vol. 16, No. 8, 24 Aug. 1981, pp. 564–570.

Stout et al., J. Med. Chem., 27 (1984), pp. 1347–1350.

*Primary Examiner*—Alan L. Rotman
*Attorney, Agent, or Firm*—Gildo E. Fato

[57] ABSTRACT

The present invention relates to new compounds of the formula

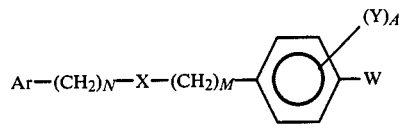

where X is

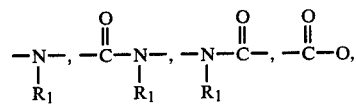

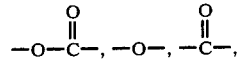

alkylene, or —S—where $R_1$ is hydrogen, alkyl, or aryl; W is hydrogen, hydroxy, amino, alkyloxy, aryloxy, O-alkyl, or O-aralkyl; $(Y)_A$ is —CH$_2$NR$_2$R$_3$ where $R_2$ and $R_3$ may be hydrogen, substituted alkyls, aryls, or together with N form a 5 to 7 membered heterocyclic group; and Ar is a substituted or unsubstituted heteroaryl. These compounds are useful in the treatment of various cardiac arrhythmias.

17 Claims, No Drawings

CERTAIN PYRIDYL SUBSTITUTED AMINOMETHYL BENZENE DERIVATIVES HAVING ANTI-ARRHYTHMIC ACTIVITY

BACKGROUND OF THE INVENTION

This application is a division of application Ser. No. 401,752, filed July 26, 1982, now U.S. Pat. No. 4,466,965, issued Aug. 21, 1984.

Cardiac arrhythmias represent a clinically significant disorder of the normal rhythm of the heart and usually require immediate and specific therapy. A common cause of cardiac arrhythmias is coronary artery disease, where a high incidence of arrhythmias has been observed during acute myocardial infarction. Premature ventricular contractions and sinus tachycardia are among the most common types of arrhythmias associated with myocardial infarction. Although these and other types of arrhythmias can be suppressed by the use of antiarrhythmic agents, the prevention of the recurrence of tachyarrhythmias is often necessary for long periods of time or even indefinitely. Consequently, these antiarrhythmic drugs must not only be effective and reliable, but they must have a minimal number of adverse side-effects associated therewith.

The heart is endowed with a specialized excitatory system for generating rhythmical impulses that cause rhythmical contraction of the heart muscle and conductive system for conducting these impulses throughout the heart. A major portion of cardiac disorders is based on abnormalities of this specialized excitatory and conductive system resulting in irregular sinus rhythm. Cardiac arrhythmias as described above, and in particular tachyarrhythmias, are caused by disorders of electrical impulse formation, by disturbances in impulse conduction, or by a combination of the two. Drugs used to treat tachyarrhythmias generally reduce or suppress excitation of the heart muscle by depressing spontaneous diastolic depolarization, and affect conduction by altering the conduction velocity through the myocardial tissue and the duration of the refractory period.

Antiarrhythmic drugs are generally administered on a long-term basis to maintain normal sinus rhythm after electrical cardioversion after normal cardiac action has been restored as alluded to above. Quinidine, 6-methoxy-α-(5′-vinyl-2-quinuclidinyl)-4-quindinemethanol and disopyramide, α[2-(diisopropylamino)-ethyl]α-phenol-2-pyridineacetamide are two antiarrhythmic agents which depress impulse formation, slow conduction velocity, and increase the duration of the refractory period of cardiac cells; and thus are useful in the treatment of supraventricular and ventricular tachyarrhythmias. However, in addition to the direct effect on the cardiac rhythm, both of these agents exhibit indirect anticholinergic actions which may affect the vagal stimulation of the heart and have an effect on peripheral parasympathetic stimulation.

Both quinidine and disopyramide exhibit adverse side-effects when administered to patients for the management of arrhythmias. The side-effects associated with quinidine include, inter alia, cardiotoxicity, diarrhea, nausea, vomiting, fever, hypertension and depression of myocardial contractility. Likewise, the side effects associated with disopyramide include, inter alia, dryness of the mouth, blurred vision, constipation, and urinary retention, and depression of myocardial contractility.

Changrolin, 4-[3′,5′-bis[N-pyrolidinylmethyl]-4′-hydroxyanilino]-quinazoline, an effective antiarrhythmic agent, also possesses substantial anticholinergic activity together with the ability to cause skin discoloration in some patients.

Heretofore, there has not been an effective antiarrhythmic agent available that has not been plagued by one or more of these unwanted, adverse side-effects, many of which are caused by excessive anticholinergic activity. In accordance with the present invention, disclosed are compounds having effective antiarrhythmic activity with less of the unwanted anticholinergic activity associated with these antiarrhythmic drugs.

SUMMARY OF THE INVENTION

In accordance with the present invention, disclosed herein are compounds of the formula

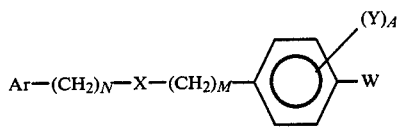

wherein X is

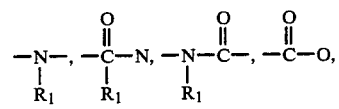

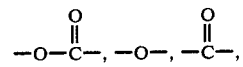

lower straight chained alkylene, or —S— wherein $R_1$ is hydrogen, aryl, or lower alkyl; W is hydrogen, hydroxy, amino,

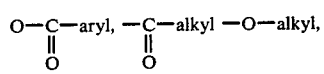

alkylsulfonamide or —O— aralkyl; $(Y)_A$ is positioned ortho to W and is an aminoalkyl having the formula —CH$_2$NR$_2$R$_3$, wherein $R_2$ and $R_3$ may together with N form a 5- to 7-membered heterocyclic group optionally including oxygen, nitrogen, or sulfur as a second heteroatom, and A is 1 or 2; N and M are independently from 0 to about 5; and Ar is a substituted or unsubstituted aryl is selected from the group consisting of pyridine, pyridazine, pyrimidine or pyrazine; where pyridine is optionally fused with one or more hteroaryls, pyridazine is optionally fused with one or more aryls, and pyrazine is optionally fused with or more aryls; and the pharmaceutically acceptable salts thereof, which are useful as cardiac antiarrhythmics.

BRIEF DESCRIPTION OF THE INVENTION

The compounds in accordance with the present invention are structurally generally characterized by two aromatic regions coupled through a linkage region as shown below.

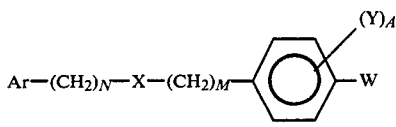

The first aromatic region

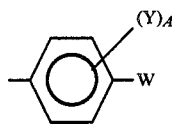

includes a para-substituted phenyl group having one or two alkyl- or arylaminomethyl substituents positioned adjacent (ortho) thereto. The para-substituent W may be hydrogen, hydroxy, amino,

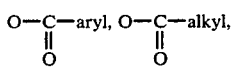

—O—alkyl, or —O—aralkyl when A is 2; and hydroxy, amino,

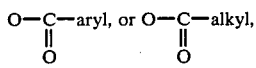

—O—alkyl, alkylsulfonamide or —O—aralkyl when A is 1. Preferably W is hydroxy, amino,

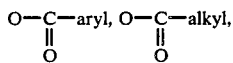

—O—alkyl, or —O—aralkyl when A is either 1 or 2. Illustrative of W substituents having the formula

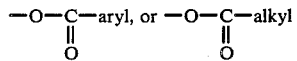

are those including but not limited to lower acyloxy groups such as acetoxy, propionyloxy, butyryloxy, and aryloxy groups such as benzoyloxy, and the like. Illustrative of W substituents having the formula —O—alkyl or —O—aralkyl are those including but not limited to lower alkyloxy and aralkyloxy groups such as methoxy, ethoxy, propoxy, butoxy, benzyloxy, phenethyloxy, phenepropyloxy, and the like. In accordance with the present invention, we have advantageously found para-hydroxy substituents effective as antiarrhythmics; thus W is most preferably hydroxy.

The alkyl or arylaminomethyl substituents of the present invention are represented by the general formula —$CH_2NR_2R_3$, where $R_2$ and $R_3$ are the same or different and may be hydrogen, lower alkyl, hydroxyalkyl such as hydroxylated straight or branched chain lower alkyl radicals, cycloalkyl, aryl, alkoxy, aralkoxy, alkoxyaryl, or heteroaryl. In the case where $R_2$ and $R_3$ are both hydrogen, it may be necessary to employ conventional blocking reagents to the amine during preparation of these compounds which are removed after the coupling of the amino substituents as set forth below. Moreover, $R_2$ and $R_3$ cannot both be alkoxy since compounds of this type would be unstable. Illustrative of alkyl- or arylaminomethyl substituents having the formula —$CH_2NR_2R_3$ are those including but not limited to those where $R_2$ and $R_3$ are methyl, ethyl, propyl, butyl, ethanol, 2-propanol, 3-propanol, butanol, methoxy, ethoxy, phenoxy, benzyloxy, cyclopenyl, cyclohexane, cycloheptyl, phenyl, benzyl, thiophene, furan, pyrole, pyran, thiphan, pyrrolidine, piperidine, morpholine, piperazine, thiomorpholine, and thioxane.

In accordance with one embodiment of the present invention, we have advantageously found that alkylaminomethyl substituents such as dimethylaminomethyl are effective as antiarrhythmics; thus they are preferred alkylaminomethyls. Alternatively, $R_2$ and $R_3$ may together with N form a 5 to 7 membered saturated or unsaturated heterocyclic group optionally including oxygen, nitrogen, or sulfur as a second heteroatom, each which may be substituted or unsubstituted. Illustrative of heterocyclic groups formed with N are those including but not limited to pyrrolidine, piperidine, morpholine, pyridine, pyrrole, piperazine, thiomorpholine, and the like. In accordance with one embodiment of the present invention, we have advantageously found alkylaminomethyl substituents where $R_2$ and $R_3$ form heterocycles with N such as pyrrolidine, piperidine, and morpholine more effective as antiarrhythmics than dimethylaminomethyl; thus these are more preferred. The most preferred heterocyclic aminomethyl substituent is pyrrolidine.

In accordance with one embodiment of the present invention, we have advantageously and unexpectedly found that bis-aminomethyl (A=2) substituted compounds exhibit greater antiarrhythmic activity than mono-aminomethyl (A=1) substituted compounds; and thus the bis-aminomethyl substituted compounds are most preferred.

In accordance with a preferred embodiment of the present invention, effective antiarrhythmic compounds were made which lack a parahydroxyl substituent (W) and thus lack in part the ability for extended conjugation of the phenol through the aryl group (Ar). We contemplate that skin discoloration associated with changrolin is due to the oxidation of the aminophenol moiety to a quinone-like structure which could result in the formation of a strong chromophore which is deposited in the skin. Thus, in accordance with one embodiment of the present invention, the W substituent should be incapable of forming such a chromophore, and is preferably hydrogen. Preferably, when W is hydrogen, the aromatic group is bis-aminomethyl (A=2).

The second region of interest for the compounds of the present invention is the aryl group (Ar) which may either be unsubstituted or substituted with various chemical substituents, or may be optionally fused with one or more aromatic groups. In accordance with the present invention, we have found that antiarrhythmic activity is lost although anticholinergic activity was maintained in the absence of the aryl (Ar) as demonstrated by the inactivity of the unsubstituted or acetyl-substituted para-aminophenol derivative.

In accordance with the present invention, the aryl group may be a 6-membered heteroaryl group having one or more nitrogens as the heteroatom. Heteroaryl compounds in accordance with the present invention include pyridine, pyridazine, pyrimidine, or pyrazine, each of which is optionally fused with one or more aryls. Illustrative heteroaryls in accordance with the present invention are those including, but not limited to pyridine, pyridazine, pyrazine, pyrimidine, quinoline, acridine, isoquinoline, phthalazine, cinnoline, pteridine, quinoxaline. Preferably, the heteroaryl is selected from the group consisting of pyridine, pyridazine, pyrazine, pyrimidine, phthalazine, quinoline, isoquinoline, quinoxaline and cinnoline. More preferably, the heteroaryl is selected from the group consisting of pyridine, pyridazine, pyrimidine, phthalazine, quinoline and isoquinoline.

Illustrative of fused aryls in accordance with the present invention are those including, but not limited to, pyridine fused with phenyl, 6-membered heteroaryls, such as pyridine, pyridazine, pyrimidine, pyrazine or 5-membered heteroaryls, such as pyrrole, imidazole, pyrazole, oxazole, thiazole, furan, thiophene and the like; pyridazine fuse with phenyl, 6-membered heteroaryls, such as pyridine, pyridazine, pyrimidine, pyrazine or 5-membered heteroaryls, such as pyrrole, imidazole, pyrazole, oxazole, thiazole, furan, thiophene and the like; pyrimidine fused with phenyl, 6-membered heteroaryls, such as pyridine, pyridazine, pyrimidine, pyrazine or 5-membered heteroaryls, such as pyrrole, imidazole, pyrazole, oxazole, thiazole, furan, thiophene and the like; pyrazine fused with phenyl, 6-membered heteroaryls, such as pyridine, pyridazine, pyrimidine, pyrazine or 5-membered heteroaryls, such as pyrrole, imidazole, pyrazole, oxazole, thiazole, furan, thiophene and the like.

In accordance with the present invention, the fused or unfused aryls may be unsubstituted, or substituted with various chemical substituents. Illustrative of substituents are those including but not limited to halogen, lower alkyl, lower alkoxy, haloalkyl such as trifluoromethyl, amino, aminoalkyl such as aminomethyl and aminoethyl, alkylamino, cyano, carbamoyl, amido, hydroxy, cycloalkyl, lower alkenyl, lower alkynyl, or phenyl. Preferred substituents are halogen such as chlorine, lower alkyl such as methyl, lower alkoxy such as methoxy, and haloalkyl such as trifloromethyl.

The third region of interest is the covalent linkage $-(CH_2)_N-(X)-(CH_2)_M-$ between the aromatic groups. In accordance with the present invention, this linkage will tolerate modification without significant loss of pharmacological activity. Linkage portions in accordance with the present invention may be those where x is

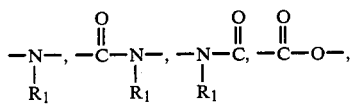

lower straight chained alkylene, or sulfur, where $R_1$ is hydrogen, lower alkyl, or aryl such as phenyl, substituted phenyl, benzyl, substituted benzyl, or heteroaryls. Preferably, x is

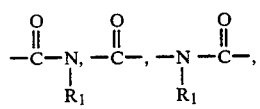

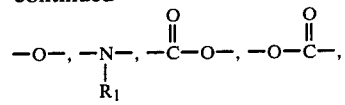

or —O— where $R_1$ is hydrogen or lower alkyl with hydrogen being most preferred. More preferred in accordance with the present invention are linkages where x is

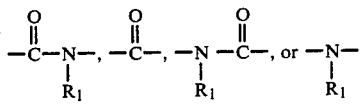

where $R_1$ is hydrogen or lower alkyl with hydrogen being most preferred. The most preferred linkages in accordance with the present invention is where x are

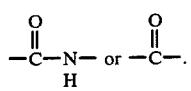

The alkylene groups in the linkage portion of these compounds may independently have from 0 to about 5 carbon atoms, and are preferably from 0 to about 2. More preferably, the linkage is such that M+N is 0, 1, or 2; and is most preferable where M+N is 0 or 1 such that M is either 0 or 1 and N is 0. Thus, illustrative linkage portions having the formula $-(CH_2)_N-X-(CH_2)_M-$ are those including but not limited to X, $-CH_2X-$, $-XCH_2-$, $-CH_2CH_2X-$, $-CH_2XCH_2-$ $-XCH_2CH_2$; such as

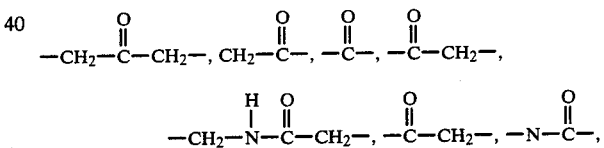

$CH_2-O-CH_2$, $-O-$, $-CH_2O$, $-OCH_2-$,

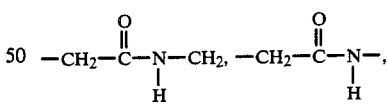

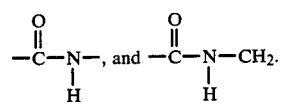

Illustrative preferred compounds in accordance with the present invention include but are not limited to those represented by the list below where W is hydroxy; $(Y)_A$ is independently and preferrably pyrrolidinylmethyl, piperidinylmethyl or morpholinomethyl; A is 2; $H_1$ is carbon, oxygen, nitrogen, or sulfur; Z is hydrogen or other substituent; *N is a 6-membered heteroaryl containing 1 or 2 nitrogen atoms; and the heteroaryl is bonded to the linkage portion indicated by either a solid or dotted line (preferred).

| Heteroaryl | —(CH$_2$)$_N$— | —X— | —(CH$_2$)$_M$— |
|---|---|---|---|
| ![pyridine with Z] | N = 0 or 1 | $-\overset{O}{\underset{\|}{C}}-$, $-\overset{O}{\underset{\|}{C}}-O-$, $-\overset{O}{\underset{\|}{C}}-\underset{H}{N}-$, $-\underset{H}{N}-$, $-\underset{H}{N}-\overset{}{\underset{\|}{C}}-$ with $=O$ | M = 0, 1, or 2 |
| ![quinoline with Z] | N = 0 or 1 | same set | M = 0, 1, or 2 |
| ![bicyclic with *N$_{1\,or\,2}$] | N = 0 or 1 | same set | M = 0, 1, or 2 |
| ![5,6-fused pyridine with H's and Z] | N = 0 or 1 | same set | M = 0, 1, or 2 |
| ![pyridazine with Z] | N = 0 or 1 | same set | M = 0, 1, or 2 |
| ![cinnoline with Z] | N = 0 or 1 | same set | M = 0, 1, or 2 |
| ![bicyclic pyridazine with *N$_{1\,or\,2}$] | N = 0 or 1 | same set | M = 0, 1, or 2 |
| ![fused pyridazine with H's and Z] | N = 0 or 1 | same set | M = 0, 1, or 2 |
| ![pyrimidine with Z] | N = 0 or 1 | same set | M = 0, 1, or 2 |

-continued

| Heteroaryl | $-(CH_2)_N-$ | $-X-$ | $-(CH_2)_M-$ |
|---|---|---|---|
| Z—[quinazoline] | N = 0 or 1 | $-\overset{O}{\underset{\|}{C}}-$, $-\overset{O}{\underset{\|}{C}}-O-$, $-\overset{O}{\underset{\|}{C}}-\underset{H}{N}-$, $-\underset{H}{N}-$, $-\underset{H}{N}-\overset{H}{\underset{\|}{C}}-$ | M = 0, 1, or 2 |
| *N$_{1\ or\ 2}$—[fused quinazoline] | N = 0 or 1 | $-\overset{O}{\underset{\|}{C}}-$, $-\overset{O}{\underset{\|}{C}}-O-$, $-\overset{O}{\underset{\|}{C}}-\underset{H}{N}-$, $-\underset{H}{N}-$, $-\underset{H}{N}-\overset{H}{\underset{\|}{C}}-$ | M = 0, 1, or 2 |
| Z—[imidazo-pyrimidine] | N = 0 or 1 | $-\overset{O}{\underset{\|}{C}}-$, $-\overset{O}{\underset{\|}{C}}-O-$, $-\overset{O}{\underset{\|}{C}}-\underset{H}{N}-$, $-\underset{H}{N}-$, $-\underset{H}{N}-\overset{H}{\underset{\|}{C}}-$ | M = 0, 1, or 2 |
| Z—[pyrazine] | N = 0 or 1 | $-\overset{O}{\underset{\|}{C}}-$, $-\overset{O}{\underset{\|}{C}}-O-$, $-\overset{O}{\underset{\|}{C}}-\underset{H}{N}-$, $-\underset{H}{N}-$, $-\underset{H}{N}-\overset{H}{\underset{\|}{C}}-$ | M = 0, 1, or 2 |
| Z—[quinoxaline] | N = 0 or 1 | $-\overset{O}{\underset{\|}{C}}-$, $-\overset{O}{\underset{\|}{C}}-O-$, $-\overset{O}{\underset{\|}{C}}-\underset{H}{N}-$, $-\underset{H}{N}-$, $-\underset{H}{N}-\overset{H}{\underset{\|}{C}}-$ | M = 0, 1, or 2 |
| *N$_{1\ or\ 2}$—[fused quinoxaline] | N = 0 or 1 | $-\overset{O}{\underset{\|}{C}}-$, $-\overset{O}{\underset{\|}{C}}-O-$, $-\overset{O}{\underset{\|}{C}}-\underset{H}{N}-$, $-\underset{H}{N}-$, $-\underset{H}{N}-\overset{H}{\underset{\|}{C}}-$ | M = 0, 1, or 2 |
| Z—[imidazo-pyrazine] | N = 0 or 1 | $-\overset{O}{\underset{\|}{C}}-$, $-\overset{O}{\underset{\|}{C}}-O-$, $-\overset{O}{\underset{\|}{C}}-\underset{H}{N}-$, $-\underset{H}{N}-$, $-\underset{H}{N}-\overset{H}{\underset{\|}{C}}-$ | M = 0, 1, or 2 |
| Z—[phthalazine/isoquinoline-N] | N = 0 or 1 | $-\overset{O}{\underset{\|}{C}}-$, $-\overset{O}{\underset{\|}{C}}-O-$, $-\overset{O}{\underset{\|}{C}}-\underset{H}{N}-$, $-\underset{H}{N}-$, $-\underset{H}{N}-\overset{H}{\underset{\|}{C}}-$ | M = 0, 1, or 2 |
| *N$_{1\ or\ 2}$—[fused phthalazine] | N = 0 or 1 | $-\overset{O}{\underset{\|}{C}}-$, $-\overset{O}{\underset{\|}{C}}-O-$, $-\overset{O}{\underset{\|}{C}}-\underset{H}{N}-$, $-\underset{H}{N}-$, $-\underset{H}{N}-\overset{H}{\underset{\|}{C}}-$ | M = 0, 1, or 2 |

| Heteroaryl | $-(CH_2)_N-$ | $-X-$ | $-(CH_2)_M-$ |
|---|---|---|---|
| | N = 0 or 1 | $\underset{\|}{\overset{O}{-C-}}, \underset{\|}{\overset{O}{-C}}-O-, \underset{H}{\underset{\|}{\overset{O}{-C}-N-}},$ $\underset{H}{-N-}, \underset{H}{-N-}\underset{\|}{\overset{\|}{C-}}$ | M = 0, 1, or 2 |

The compounds of the present invention and equivalents thereof possessing substantially similar pharmacological property may be prepared according to several general schemes as set forth below.

SCHEME I

The arylamide derivatives of the substituted amino-

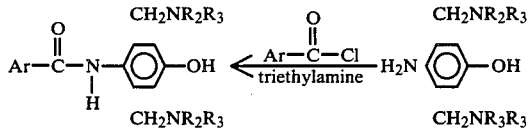

phenols are prepared by aminomethylation of acetominophen by the Mannich reaction, removing the acetyl group and reacting the aniline derivative with the appropriate aromatic acid chloride.

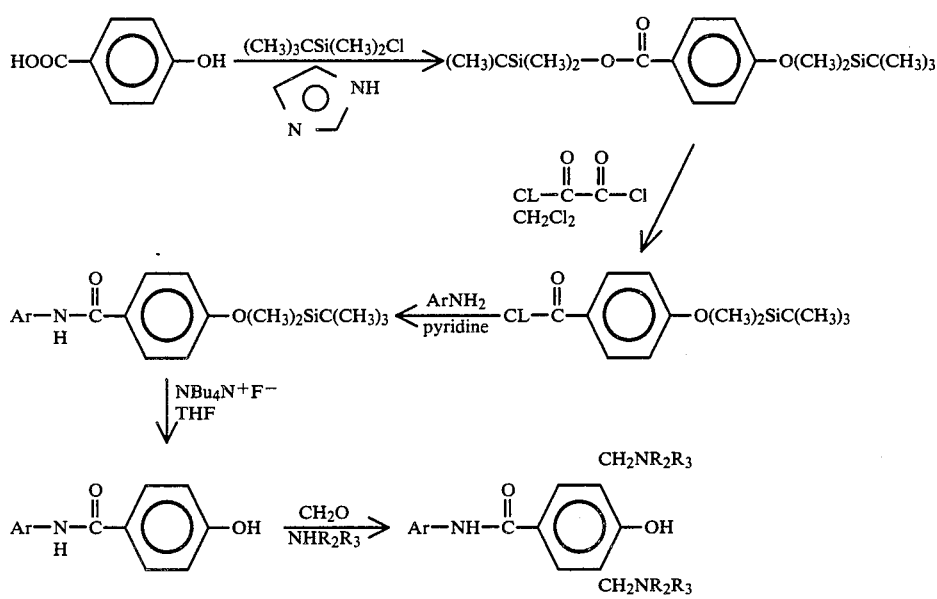

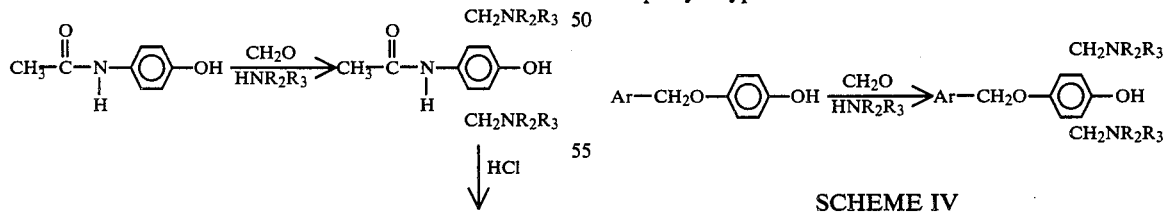

SCHEME III

The aryloxy derivatives of the substituted aminophenols are prepared by aminomethylation of the appropriate p-aryloxyphenol.

SCHEME IV

The keto derivatives of the substituted phenols are prepared by aminomethylation of the appropriate p-hydroxybenzo-aryl ketone.

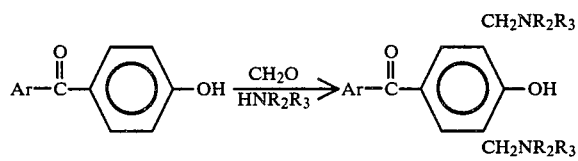

Scheme IVa
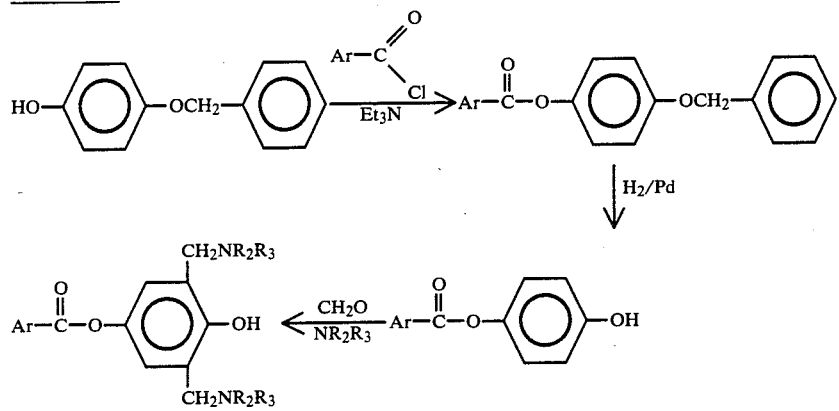
Scheme IVb
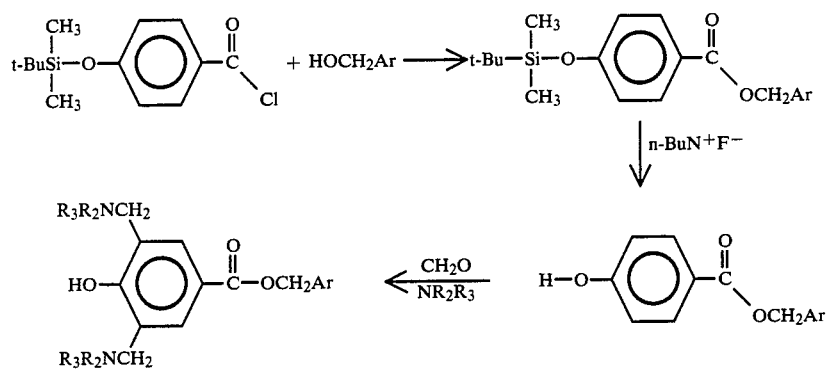
SCHEME V
Aryl amide derivatives of the substituted phenols are prepared by demethylation of p-methoxybenzylamine followed by reaction with the appropriate aromatic acid chloride and aminomethylation.
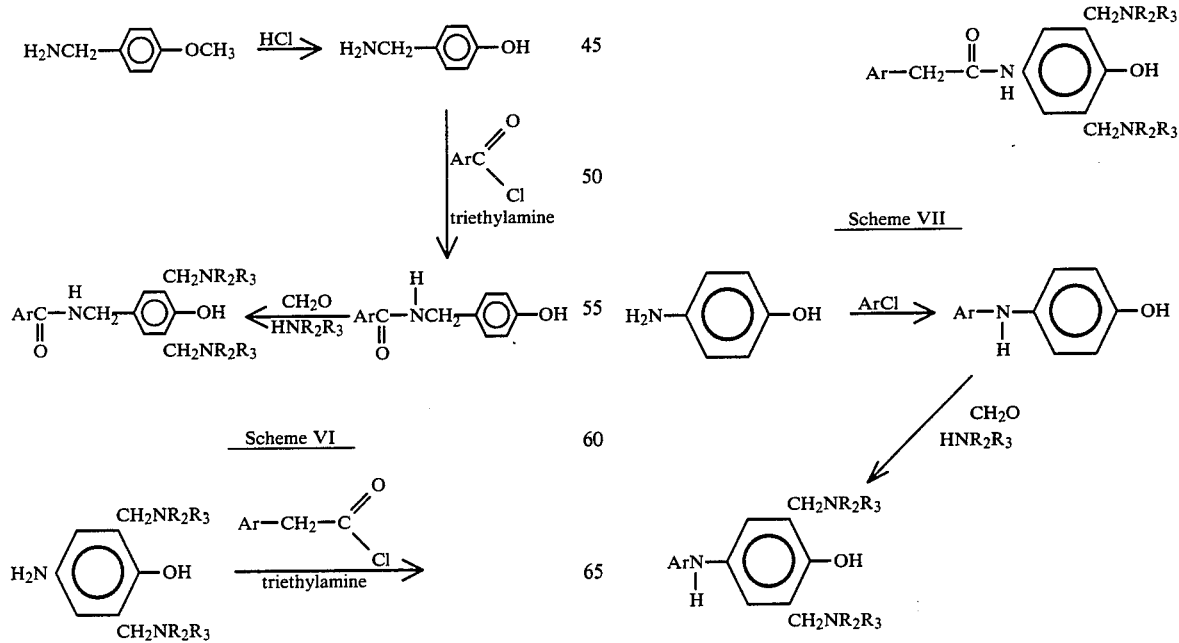
Scheme VI
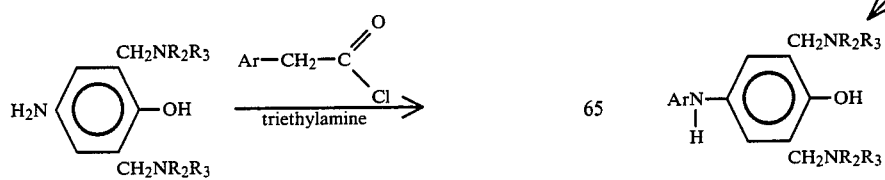
-continued
Scheme VI
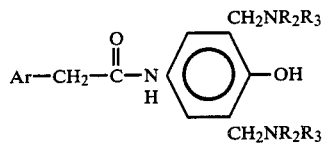

Scheme VIII
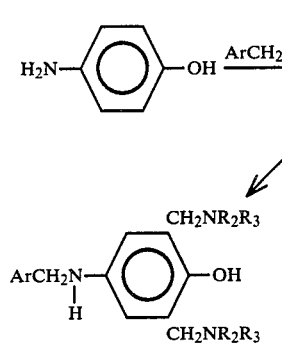
Scheme IX
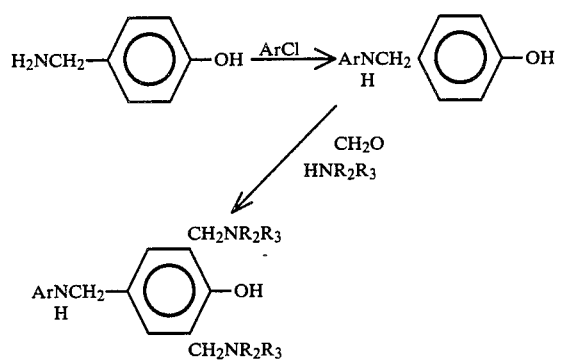
Scheme X
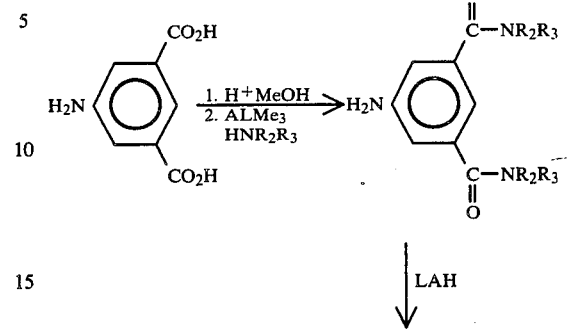
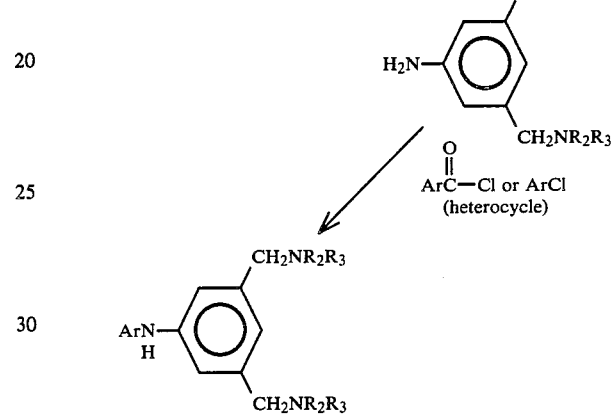
Scheme XI
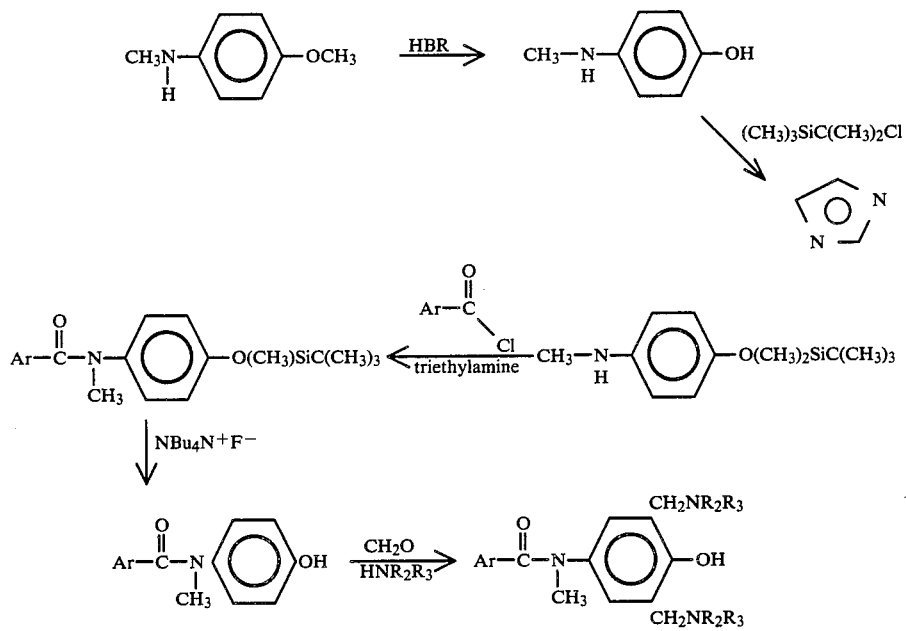
The mono-substituted aminoalkyl compounds in accordance with the present invention are co-produced with the di-substituted compounds and are separated from the di-substituted compounds by medium pressure liquid chromatography (MPLC) on silica gel columns.

The compounds of the present invention possess advantageous pharmacological properties useful for the treatment of cardiac arrhythmias, and in particular for the suppression of supraventricular and ventricular tachyarrthmias. It is contemplated that these compounds, in addition to maintaining normal sinus rhythm by supression of tachyarrhythmia, will be most useful prophylactically for the prevention of premature ventricular complex formation in human patients on long-term therapy. Further, in accordance with the present invention, we have found that these compounds effectively suppress ventricular arrhythmias when administered orally or parenterally by infusion to dogs, while unexpectedly exhibiting a benefically low anticholinergic activity in guinea pig illeum tests. These compounds also exhibit superior antiarrhythmic properties to other known antiarrhythmic agents. Thus, the desirable antiarrhythmic potency of these compounds is maximized in relationship to the undesirable side-effects associated with anticholinergic activity. It is further contemplated that these compounds can be used as antimalarials.

The compounds in accordance with the present invention are made pharmacologically compatible, for example, by the neutralization of the free amine groups thereof with non-toxic pharmaceutically acceptable inorganic or organic salts by conventional methods. Pharmaceutically acceptable salts of these compounds are illustrated by those including but not limited to hydrochloric acid, sulfuric acid, phosphoric acid, hydrobromic acid, acetic acid, lactic acid, citric acid, oxalic acid, malic acid, salicylic acid, and the like. Further, the pharmaceutically acceptable salts of compounds in accordance with the present invention may be used in admixture with a conventional solid or liquid pharmaceutical carrier or diluent. These compositions may be administered orally or parentally by conventional methods. For oral administration, fine powders or granules of the compound may contain diluents, binders, lubricants, and dispersing and surface active agents, and and the like may be in the dried state in coated or uncoated tablets, or in suspension. For parenteral administration, the compounds may be in aqueous injection or infusion solutions which may contain antioxidants, buffers, bacteriostats, solubilizing agents, and the like or solutes which render the salts isotonic with the blood such as in isotonic saline.

The dosage of the novel compounds of the present invention depends on several factors, as determined for conventional antiarrhythmic agents. Dosages ranging from 1 to 20 mg per kg of body weight were found to be effective in adult mongrel dogs (10–65 kg) when infused intravenously at a cumulative rate of 0.3 mg/kg/min.

The following examples are intended to be illustrative of the present invention but should not be considered as limiting the scope thereof:

EXAMPLE I 3,5-bis(N-pyrrolidinylmethyl)-4-hydroxyaniline

This example describes the synthesis of a compound having the formula

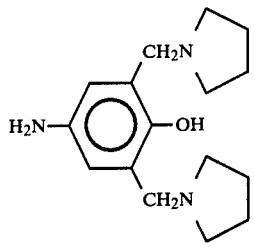

A solution of 100.0 g (0.315 mol) of 3',5'-bis(N-pyrrolidinylmethyl)-4-hydroxyacetanilide in 200 ml of 6 MHCl was heated to reflux for 3 hours. The solution was basified with solid KOH to a pH of 11. The resulting solid was collected by filtration and washed with water and cold ether. Crystallization from ether yielded pale yellow needles: mp 100°–105° C. The HCl salt formed white crytals: mp 219°–221° C. The IR and NMR spectra were consistent with the assigned structure and the elemental analysis was consistent with the empirical formula ($C_{16}H_{25}N_3O$).

EXAMPLE II 4-(4'-hydroxyanilino)-quinazoline

This example describes the synthesis of a compound having the formula

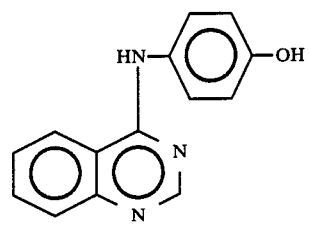

This compound was prepared as described by Liangguan, L.; Zhixiang, Q.; Zhimin, W.; Yanlin, Z.; Guangsheng, D.; Guojum, H.; and Zueyi, Y. in *Scientia Sinica*, 22, 1220 (1979: mp 249°–251° C.

EXAMPLE III 1-(4'-hydroxyanilino)phthalazine

This example describes the synthesis of a compound having the formula

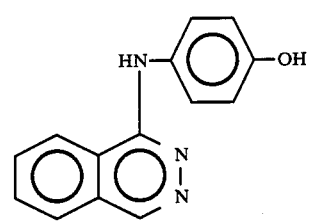

A mixture of 2.00 g (12.1 mmol) of 1-chlorophthalazine and 2.64 g (24.2 mmol) of p-aminophenol in 40 ml of absolute ethanol was heated to reflux for 2 h. The precipitate was collected and successively washed with a saturated solution of $NaHCO_3$ and water. The product was crystallized from methanol: mp 245°–247° C. The HCl salt had a mp > 300° C.; the IR and NMR spectra were consistent with the assigned structure and the elemental analysis was consistent with the empirical formula ($C_{14}H_{11}N_3O \cdot HCl$).

EXAMPLE IV

1[3',5'-bis[N-pyrrolidinylmethyl]-4'-hydroxyanilino]-phthalazine

This example describes the synthesis of a compound having the formula

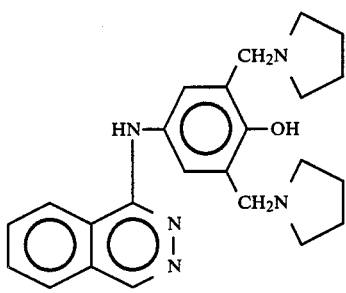

A mixture of 4.65 g (19.5 mmol) of the compound prepared according to Example III, 6.5 ml of a 37% solution of formaldehyde and 4.5 mL (54 mmol) of pyrrolidine in 3 mL of ethanol was stirred with warming for 3 h. The solvent was removed on a rotary evaporator, the product was dissolved in CHCl$_3$, the solution was washed with water, dried (MgSO$_4$) and saturated with dry hydrogen chloride. The solvent was removed and crystallization was effected with isopropanol/ether, leaving bright yellow crystals: mp 183°-185° C. The IR and NMR spectra were consistent with the assigned structure, and the elemental analysis was consistent with the empirical formula ($C_{24}H_{20}N_5O \cdot 3HCl \cdot H_2O$).

EXAMPLE V

1-N-[3',5'-bis(N-pyrrolidinylmethyl)-4'-hydroxyanilino]-4-chlorophthalazine

This example describes the synthesis of a compound having the formula

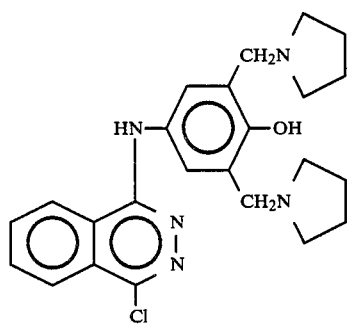

A mixture of 51.4 g of 1,4-dichlorophthalazine and 28.2 g of p-aminophenol in 750 ml of absolute ethanol was heated to reflux for 10 hours. The precipitate was collected and successively washed with a saturated solution of NaHCO$_3$ and water. A mixture of 56.8 g of this product, 42 ml of a 37% solution of formaldehyde and 62 ml of pyrrolidine in 3 ml of ethanol was stirred with warming for 3 hours. The solvent was removed on a rotary evaporator, the product dissolved in CHCl$_3$, the solution washed with water, dried (MgSO$_4$) and saturated with dry hydrogen chloride. The solvent was removed, purified by MPLC on silice gel (EtOAc/MeOH/NH$_4$OH 9:1:0.01) and crystallization was effected with isopropanol/ether affording pale yellow crystals: mp 169°-170° C. The IR and NMR spectra were consistent with the assigned structure and the elemental analysis was consistent with the emperical formula ($C_{24}H_{28}ClN_5O$).

EXAMPLE VI

1-N-[3'-N-pyrrolidinylmethyl-4'-hydroxyanilino]-4-chlorophthalazine

This example describes the synthesis of the following compound:

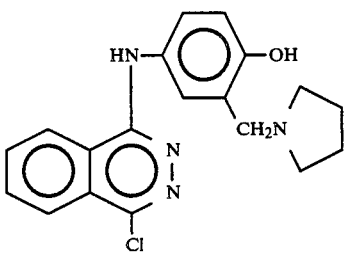

The compound was prepared identically to the compound of Example V with the exception that it was separated therefrom by MPLC chromatography: mp 157°-158° C. The IR and NMR spectra were consistent with the assigned structure, and the elemental analysis was consistent with the empirical formula ($C_{19}H_{19}N_4OCl$).

EXAMPLE VII

1-N-[3',5'-bis(pyrrolidinylmethyl)-4'-hydroxyanilino]-4-methoxyphthalazine

This example describes the synthesis of the following compound

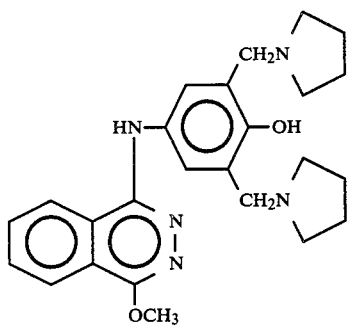

A mixture of 2.7 g (6.2 mmol) of the compound prepared according to Example V and 3.7 g (69 mmol) of freshly prepared NaOMe (1.58 g Na and MeOH) was heated to 120° C. for 18 hours, cooled and quenched with water. Purification by MPLC on silica gel (EtOAc/MeOH/NH$_4$OH, 1:1:0.01) and crystallized from CHCl$_3$/EtOAc, affording yellow crystals: mp 178°-179° C. The IR and NMR spectra were consistent with the assigned structure, and the elemental analysis was consistent with the empirical formula ($C_{25}H_{31}NO_2 \cdot H_2O$)

EXAMPLE VIII

1-N-[3′,5′-bis(pyrrolidinylmethyl)-4′-hydroxyanilino]-isoquinoline

This example describes the synthesis of the following compound:

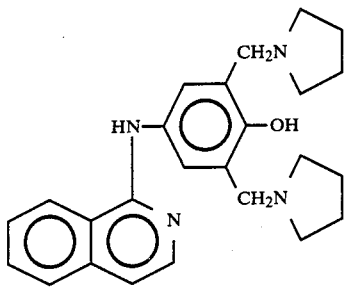

A mixture of 3 g of 1-chloroisoquinoline and 2 g of p-aminophenol in 40 ml of absolute ethanol was heated to reflux for 4 hours. The precipitate was collected and successively washed with a saturated solution of NaHCO$_3$ and water, and the product crystallized from methanol. A mixture of 3.8 g of this product, 36 ml pyrrolidine and 3.3 ml of 37% solution of formaldehyde in 50 ml of ethanol and was stirred with warning for 3 hours. The solvent was removed on a rotary evaporator, the product was dissolved in CHCl$_3$, the solution was washed with water, dried (MgSo$_4$) and saturated with dry chloride. The solvent was removed and crystallization was effected with isopropanol/ether leaving bright yellow crystals: MP 95° C. The IR and NMR spectra were consistent with the assigned structure, and the elemental analysis was consistent with the empirical formula (C$_{25}$H$_{30}$N$_4$O.HCl.H$_2$O)

EXAMPLE IX

1-[3′,5′-bis[(N,N-dimethyl)aminomethyl]-4′-hydroxyanilinophthalazine

This example describes the synthesis of the following compound

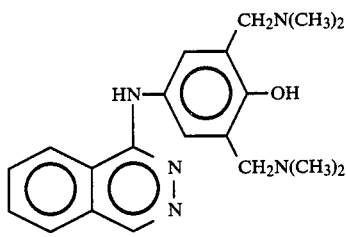

The compound was prepared as the compound according to Example IV with the exception that dimethylamine was used in place of pyrrolidine: mp 195° C. (HCl salt). The IR and NMR spectra were consistent with the assigned structure and the elemental analysis was consistent with the empirical formula (C$_{20}$H$_{25}$N$_5$O.3HCl).

EXAMPLE X

3-N-[3′,5′-bis(N-pyrrolidinylmethyl)-4′-hydroxyanilino]-6-chloropyridazine

This example describes the synthesis of the following compound

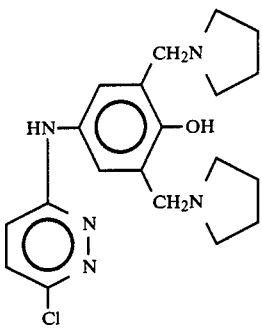

The compound was prepared as the compound according to Example IV with the exception that 3,6-dichloropyridazine was used in place of 1-chlorophthalazine: mp 150°–151° C. The IR and NMR spectra were consistent with the assigned structure and the elemental analysis was consistent with the empirical formula (C$_{20}$H$_{26}$N$_5$OCl).

EXAMPLE XI

2-N-[3′,5′-bis(pyrrolidinylmethyl)-4′-hydroxyanilino]-pyrimidine

This example describes the synthesis of a compound having the formula

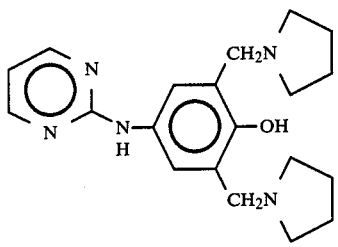

The compound was prepared as the compound according to Example IV with the exception that 2-chloropyrimidine was used in place of 1-chlorophthalazine: mp 171°–172° C. The IR and NMR spectra were consistent with the assigned structure and the elemental analysis was consistent with the empirical formula (C$_{20}$H$_{27}$N$_5$O).

EXAMPLE XII

4-[3′,5′-bis(pyrrolidinylmethyl)-4′-hydroxyanilino]-6,7,8-trimethoxyquinazoline

This example describes the synthesis of a compound having the formula

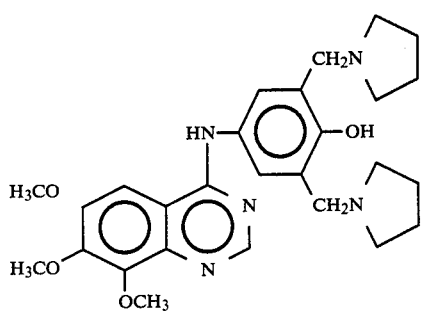

The compound was prepared as the compound according to Example IV with the exception that 4-chloro-6,7,8,-trimethoxyquinazoline was used in place of 1-chlorophthalazine: mp 189°–191° C. The IR and NMR spectra were consistent with the assigned structure and the elemental analysis was consistent with the empirical formula ($C_{27}H_{35}N_5O_4$).

EXAMPLE XIII

4-[3',5'-bis(N-pyrrolidinylmethyl)-4'-hydroxyanilino]-7-trifluoromethylquinoline This example describes the synthesis of a compound having the formula

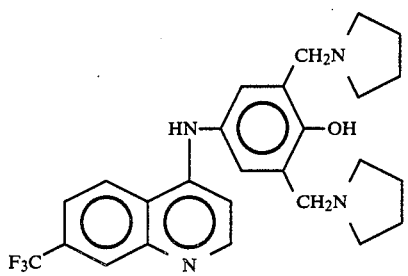

The compound was prepared as the compound according to Example IV with the exception that 4-chloro-7-trifluoromethylquinoline was used in place of 1-chlorophthalazine: mp 56°–58° C. The IR and NMR spectra were consistent with the assigned structure and the elemental analysis was consistent with the empirical formula ($C_{26}H_{29}N_4OF_3.4HCl.H_2O$).

EXAMPLE XIV 2-methyl-4-[3',5'-bis(N-pyrrolidinylmethyl)]-4'-hydroxyanilinoquinoline The following example describes the synthesis of a compound having the formula

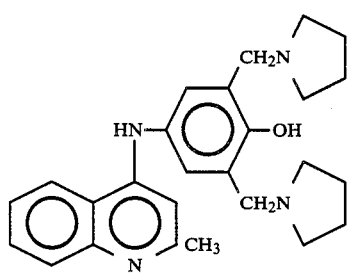

A mixture of 5.0 g (18 mmol) of the compound prepared according to Example I and 3.23 g. (18 mmol) of 2-methyl-4-chloroquinoline was heated to between 130° and 145° C. for 1 hour, making certain that the temperature did not exceed 145° C. The product was purified by MPLC ($CHCl_3/MeOH/NH_4OH$, 9:1:0.01) and recrystallized from isopropanol, yielding yellow crystals: mp 150°–155° C. (HCl salt). The IR and NMR spectra were consistent with the assigned structure and the elemental analysis was consistent with the empirical formula ($C_{26}H_{32}N_4O.HCl$).

EXAMPLE XV

4-[3',5'-bis(N-pyrrolidinylmethyl)-4'-hydroxyanilino]-7-chloroquinoline

This example describes the synthesis of a compound having the formula

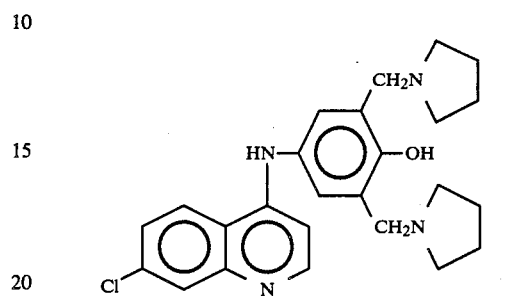

The compound was prepared as the compound according to Example XIV with the exception that 4,7-dichlorquinoline was used in place of 2-methyl-4-chloroquinoline: mp 92° C. The IR and NMR spectra were consistent with the assigned structure and the elemental analysis was consistent with the empirical formula ($C_{25}H_{29}N_4OCl.4HCl.3H_2O$).

EXAMPLE XVI

4-[3',5'-bis(N-pyrrolidinylmethyl)-4'-hydroxyanilino]-quinoline

This example describes the synthesis of a compound having the formula

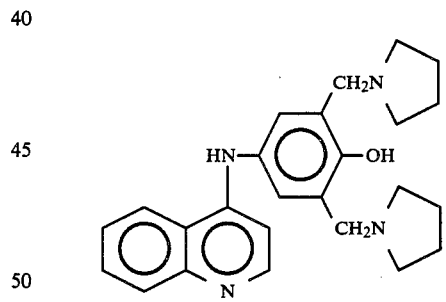

The compound was prepared as the compound according to Example XIV with the exception that 4-chloroquinoline was used in place of 2-methyl-4-chloroquinoline: mp 67° C. The IR and NMR spectra were consistent with the assigned structure and the elemental analysis was consistent with the empirical formula ($C_{25}H_{20}N_4O.4HCl.2H_2O$).

EXAMPLE XVII

2-[3',5'-bis(N-pyrrolidinylmethyl)-4'-hydroxyanilino]-quinoline

This example describes the synthesis of a compound having the formula

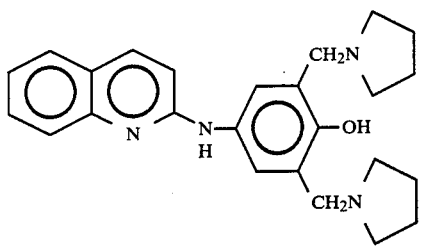

The compound was prepared as the compound according to Example IV with the exception that 2-chloroquinoline was used in place of 1-chlorophthalazine: mp 64°–66° C. The IR and NMR spectra were consistent with the assigned structure and the elemental analysis was consistent with the empirical formula (C$_{25}$H$_{30}$N$_4$O.3HCl.3H$_2$O).

EXAMPLE XVIII

2-[3'-(N-pyrrolidinylmethyl)-4'-hydroxyanilino]-quinoline

This example describes the synthesis of a compound having the formula

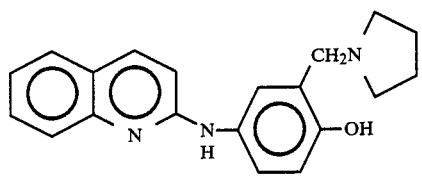

This compound was prepared as the compound according to Example XVII with the exception that it was separated therefrom as a byproduct. The IR and NMR spectra were consistent with the assigned structure and the elemental analysis was consistent with the empirical formula (C$_{20}$N$_{21}$N$_3$O.0.5H$_2$O).

EXAMPLE XIX

1-N-[3',5'-bis(N-pyrrolidinylmethyl)-4'-hydroxybenzylamino]-4-chlorophthalazine

This example describes the synthesis of a compound having the formula

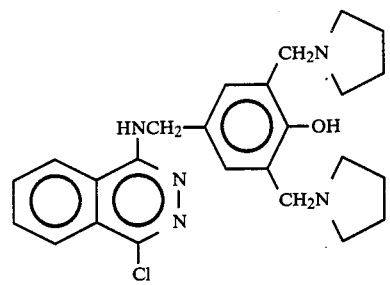

p-hydroxybenzylamine was formed by heating to reflux p-methoxybenzylamine in concentrated HCl. The solution was neutralized with solid KOH and the product was collected by filtration. The compound was prepared as the compound according to Example IV using p-hydroxybenzylamine and 1,4-dichlorophthalazine: mp 197°–199° C. The IR and NMR spectra were consistent with the assigned structure and the elemental analysis was consistent with the empirical formula (C$_{25}$H$_{30}$N$_5$OCl.3HCl.1.5H$_2$O).

EXAMPLE XX

4-N-[(3',5'-bis(pyrrolidinylmethyl)-4'-hydroxyanilino]-pyridine

This example describes the synthesis of a compound having the formula

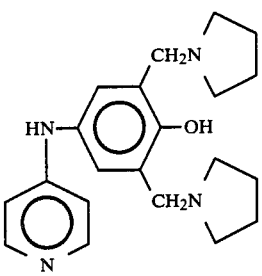

The compound was prepared as the compound of Example IV with the exception that 4-chloropyridine was used in place of 1-chlorophthalazine: mp 158°–159° C. The IR and NMR analysis were consistent with the assigned structure and the elemental analysis was consistent with the empirical formula (C$_{21}$H$_{28}$N$_4$O).

EXAMPLE XXI

4-N-[(3',5'-bis(pyrrolidinylmethyl)-anilino]-1-chlorophthalazine

This example describes the synthesis of a compound having the formula

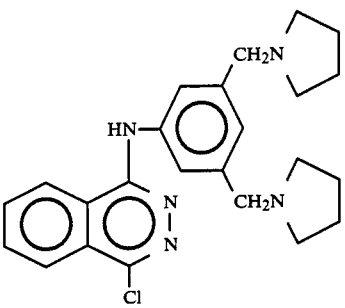

Using the procedure of Weinreb, *Tetrahedron Letters* (1977) p4171, a solution of 6.5 ml of pyrrolidine in 100 ml of CH$_2$Cl$_2$ under a nitrogen atmosphere was treated with 39 ml (78 mmol) of trimethylaluminum. After gas evolution had ceased, 8.2 g (39 mmol) of dimethyl-5-aminoisophthalate (5-aminoisophathalic acid in HCl/MeOH) was added and the solution was heated to reflux for 38 hours. The cooled solution was slowly added to ice water. The aqueous mixture was filtered and extracted with CHCL$_3$. The combined extracts were dried (MgSO$_4$) and the solvent removed, leaving 8.9 g of solid product. A mixture of 5.0 g (16 mmol) of this crude product and 2.4 g (6.3 mmol) of lithium aluminum hydride in 100 ml of ether under a nitrogen atmosphere was heated to reflux for 4 hours. The solution was cooled in an ice bath and quenched with water. The aqueous mixture was filtered and extracted with ether. The combined extracts were dried (MgSO$_4$) and the solvent removed, leaving a yellow oil. Distillation with a Kugelrohr apparatus (90° C. oven temperature, 0.1 mm) afforded a colorless oil.

A mixture of 5.00 g (19.3 mmol) of this product and 3.84 g (19.3 mmol) of 1,4-dichlorophthalazine under a nitrogen atmosphere was heated to 160° C. (oil bath temperature) for 3 hours. Purification of the product by silica gel column chromatography (CHCl$_3$/MeOH/NH$_4$OH; 9:1:0.05) afforded yellow crystals: mp 180°–183° C. The IR and NMR spectra were consistent with the assigned structure and the elemental analysis was consistent with the empirical formula (C$_{24}$H$_{28}$N$_5$Cl).

EXAMPLE XXII

The following examples describe the pharmacological evaluation of the compounds made in accordance with the present invention. In particular, these examples describe the evaluation of antiarrhythmic activity by coronary ligation in the well known Harris dog model. Ventricular arrhythmias were induced in adult mongrel dogs (10–15 kg) of either sex by two-state ligation of the left anterior descending coronary artery. On the following day a high percentage of (90–100%) of ectopic beats existed. The test compound in saline was infused intravenously at a cumulative rate of 0.3 mg/kg/min (base) until normal sinus rhythm or toxicity occurred. Normal sinus rhythm was defined as 90–100% normal complexes over a 5 min period. The results of these tests are set forth in Table I.

EXAMPLE XXIII

The following examples describe the in vitro evaluation of anticholinergic activity in the isolated guinea pig ileum. Fasted, male Hartley guinea pigs (300–400 g) were killed by a blow to the head. A 1 cm segment of ileum was removed and placed in a bath containing physiological saline solution (in mmol/L: NaCl, 120; NaHCO$_3$, 25; KCl, 4.7; MgSO$_4$, 0.57; KH$_2$PO$_4$, 1.2; CaCl$_2$, 1.96; destrose, 11.1). One end of the ileal strip was impaled onto a platinum wire electrode; and the other end was tied to a stationary glass rod. Basal tension was set at 0.1–0.3 g and peak developed tension in response to field stimulation (100–150 V, 10 msec pulse duration, 0.2 Hz) was measured with a tension transducer. Tension development was then assessed after test drug was at a concentration of 4 mg/L. Since contractile tension in this preparation is due to cholinergic activity, the percent inhibition was termed the anticholinergic activity of the drug; the greater the percent inhibition the greater the anticholinergic activity. The results of these tests are set forth in Table I.

TABLE I

| Compound (Example No.) | Antiarrhythmic ED[1] in Harris Dog (mg/kg IV) | Anticholinergic Inhibition of Guinea Pig Ileum (% inhibition at 4 mg/L) |
|---|---|---|
| I | inactive[2] | 3 |
| II | inactive[2] | 13 |
| III | inactive[2] | 23 |
| IV | 1.5 | 83 |
| V | 2.5 | 76 |
| VI | 17 | 65 |
| VII | low activity | 84 |
| VIII | 1.1 | active |
| IX | 14 | 14 |
| X | 10.5 | 40 |
| XI | low activity | 6 |
| XII | low activity | 14 |
| XIII | 3.0 | 36 |
| XIV | 9.5 | — |

TABLE I-continued

| Compound (Example No.) | Antiarrhythmic ED[1] in Harris Dog (mg/kg IV) | Anticholinergic Inhibition of Guinea Pig Ileum (% inhibition at 4 mg/L) |
|---|---|---|
| XV | low activity | 27 |
| XVI | low activity | 19 |
| XVII | 6 | 50 |
| XVIII | 11 | 72 |
| XIX | 4.5 | 78 |
| XX | 8 | 5 |
| XXI | 3 | 93 |
| Quinidine | 10.1 | 62 |
| Disopyramide | 6.8 | 81 |
| Changrolin | 10.3 | 43 |

[1]ED is the effective dose required to sustain normal sinus rhythm.
[2]No effect on sinus rhythm up to a cumulative dose of 30 mg per kg.

The present invention has been described in detail and with particular reference to the preferred embodiments; however, it will be understood by one having ordinary skill in the art that changes can be made thereto without departing from the spirit and scope thereof.

We claim:

1. A compound of the formula

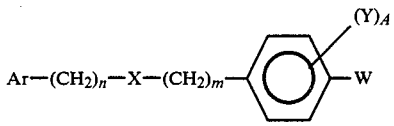

where X is

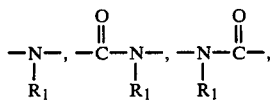

wherein R$_1$ is hydrogen, or lower alkyl; W is hydrogen, or hydroxy; (Y)$_A$ is positioned ortho to W and is an aminoalkyl having the formula —CH$_2$NR$_2$R$_3$, wherein R$_2$ and R$_3$ are the same or different and may be hydrogen, lower alkyl, or R$_2$ and R$_3$ may together with N form a pyrrolidino, piperidino, morpholino, pyridine, pyrrole, piperazino, or thiomorpholino group, and A is 2; n and m are independently from 0 to 2; and Ar is pyridine, which may be unsubstituted or substituted with chloro, lower alkyl, lower alkoxy, or trifluoromethyl, or a pharmaceutically acceptable salt thereof.

2. The compound of claim 1 wherein W is hydroxy.

3. The compound of claim 2 wherein X is

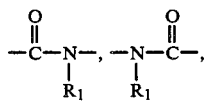

wherein R$_1$ is hydrogen.

4. The compound of claim 3 wherein X is

and m is 0.

5. The compound of claim 1 where X is $$-\underset{R_1}{N}-, -\overset{O}{\underset{\|}{C}}-\underset{R_1}{N}-, -\underset{R_1}{N}-\overset{O}{\underset{\|}{C}}-,$$

wherein R$_1$ is hydrogen;
W is hydroxy;
(Y)$_A$ is pyrrolidinomethyl, piperidinomethyl, or morpholinomethyl;
A is 2; and
n and m are each 0.

6. The compound of claim 5 wherein X is $$-\underset{R_1}{N}-$$

wherein R$_1$ is hydrogen;
W is hydroxy;
(Y)$_A$ is pyrrrolidinomethyl; and
A is 2.

7. A compound of the formula $$Ar-(CH_2)_n-X-(CH_2)_m-\underset{}{\bigcirc}\underset{W}{\overset{(Y)_A}{}}$$

where X is $$-\underset{R_1}{N}-, -\overset{O}{\underset{\|}{C}}-\underset{R_1}{N}, -\underset{R_1}{N}-\overset{O}{\underset{\|}{C}}-,$$

wherein R$_1$ is hydrogen, or lower alkyl; W is hydrogen, or hydroxy; (Y)$_A$ is positioned ortho to W and is an aminoalkyl having the formula —CH$_2$NR$_2$R$_3$, wherein R$_2$ and R$_3$ are the same or different and may be hydrogen, lower alkyl, or R$_2$ and R$_3$ may together with N form a pyrrolidino group, and A is 2; n and m are independently from 0 to 2; and Ar is pyridine, which may be unsubstituted or substituted with chloro, lower alkyl, lower alkoxy, or trifluoromethyl, or a pharmaceutically acceptable salt thereof.

8. The compound of claim 7 wherein X is $$-\underset{R_1}{N}-,$$

R$_1$ is hydrogen, (Y)$_A$ is pyrrolidinomethyl, and W is hydrogen or hydroxy.

9. A cardiac arrhythmic composition containing an antiarrhythmic-effective amount of the compound having the formula $$Ar-(CH_2)_n-X-(CH_2)_m-\underset{}{\bigcirc}\underset{W}{\overset{(Y)_A}{}}$$

where X is $$-\underset{R_1}{N}-, -\overset{O}{\underset{\|}{C}}-\underset{R_1}{N}-, -\underset{R_1}{N}-\overset{O}{\underset{\|}{C}}-,$$

wherein R$_1$ is hydrogen or lower alkyl; W is hydrogen, or hydroxy; (Y)$_A$ is positioned ortho to W and is an aminoalkyl having the formula —CH$_2$NR$_2$R$_3$, wherein R$_2$ and R$_3$ are the same or different and may be hydrogen, lower alkyl, or R$_2$ and R$_3$ may together with N form a pyrrolidino, piperidine, morpholino, pyridine, pyrrole, piperazino or thiomorpholino group and A is 2; n and m are independently from 0 to 2 and Ar is pyridine, which may be unsubstituted or substituted with chloro, lower alkyl, lower alkoxy, or trifluoromethyl; and the pharmaceutically acceptable salts thereof in admixture with a pharmaceutically acceptable carrier or diluent.

10. The composition of claim 9 wherein (Y)$_A$ is pyrrolidinomethyl, piperidinomethyl, morpholinomethyl or —CH$_2$NR$_2$R$_3$ where R$_2$ and R$_3$ are the same or different and are lower alkyl.

11. The composition of claim 10 wherein X is $$-\overset{O}{\underset{\|}{C}}-\underset{R_1}{N}-, -\underset{R_1}{N}-\overset{O}{\underset{\|}{C}}-,$$

wherein R$_1$ is hydrogen or lower alkyl.

12. The composition of claim 9 wherein X is $$-\underset{R_1}{N}-, -\overset{O}{\underset{\|}{C}}-\underset{R_1}{N}-, -\underset{R_1}{N}-\overset{O}{\underset{\|}{C}}-,$$

wherein R$_1$ is hydrogen;
W is hydroxy;
(Y)$_A$ is pyrrolidinomethyl, piperidinomethyl, or morpholinomethyl;
A is 2; and
n and m are each.

13. A cardiac arrhythmic composition containing an antiarrhythmic-effective amount of the compound having the formula $$Ar-(CH_2)_n-X-(CH_2)_m-\underset{}{\bigcirc}\underset{W}{\overset{(Y)_A}{}}$$

where X is $$-\underset{R_1}{N}-, -\overset{O}{\underset{\|}{C}}-\underset{R_1}{N}-, -\underset{R_1}{N}-\overset{O}{\underset{\|}{C}}-,$$

wherein R$_1$ is hydrogen or lower alkyl; W is hydrogen, or hydroxy (Y)$_A$ is positioned ortho to W and is an aminoalkyl having the formula —CH$_2$NR$_2$R$_3$, wherein R$_2$ and R$_3$ are the same or different and may be hydrogen, lower alkyl, or R$_2$ and R$_3$ may together with N form a pyrrolidino group and A is 2; n and m are independently from 0 to 2 and Ar is pyridine which may be unsubstituted or substituted with chloro, lower alkyl, lower alkoxy, or trifluoromethyl; and the pharmaceutically acceptable salts thereof in admixture with a pharmaceutically acceptable carrier or diluent.

14. The composition of claim 13 wherein X is

$R_1$ is hydrogen, $(Y)_A$ is pyrrolidinomethyl, and W is hydrogen or hydroxy.

15. A method of treating cardiac arrhythmias by administration of an anti-arrhythmic effective amount of a compound having the formula

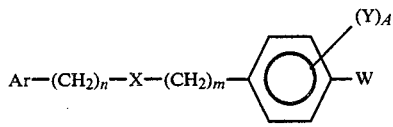

where X is

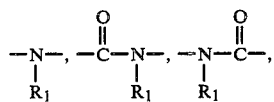

wherein $R_1$ is hydrogen or lower alkyl; W is hydrogen, or hydroxy; $(Y)_A$ is positioned ortho to W and is —$CH_2NR_2R_3$, wherein $R_2$ and $R_3$ are the same or different and may be hydrogen, lower alkyl, or $R_2$ and $R_3$ may together with N form a pyrrolidino, piperidino, morpholino, pyridine, pyrrole, piperazino or thiomorpholino group and A is 2; n and m are independently from 0 to 2; and Ar is pyridine, which may be unsubstituted or substituted with chloro, lower alkyl, lower alkoxy, or trifluoromethyl; and the pharmaceutically acceptable salts thereof.

16. A method of treating cardiac arrhythmias by administration of an anti-arrhythmic effective amount of a compound having the formula

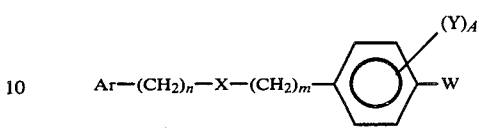

where X is

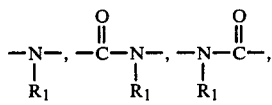

wherein $R_1$ is hydrogen or lower alkyl; W is hydrogen or hydroxy $(Y)_A$ is positioned ortho to W and is —$CH_2NR_2R_3$, wherein $R_2$ and $R_3$ are the same or different and may be hydrogen, lower alkyl, or $R_2$ and $R_3$ may together with N form a pyrrolidino group and A is 2; n and m are independently from 0 to 2; and Ar is pyridine, which may be unsubstituted or substituted with chloro, lower alkyl, lower alkoxy, or trifluoromethyl; and the pharmaceutically acceptable salts thereof.

17. The method of claim 16 wherein X is

$R_1$ is hydrogen, (Y)A is pyrrolidinomethyl, and W is hydrogen or hydroxy.

* * * * *